(12) United States Patent
Lewis

(10) Patent No.: US 10,376,035 B2
(45) Date of Patent: Aug. 13, 2019

(54) LIP BALM CONTAINER WITH DENTAL FLOSS DISPENSER

(71) Applicant: Amanda J. Lewis, Decatur, IL (US)

(72) Inventor: Amanda J. Lewis, Decatur, IL (US)

( * ) Notice: Subject to any disclaimer, the term of this patent is extended or adjusted under 35 U.S.C. 154(b) by 102 days.

(21) Appl. No.: 15/723,281

(22) Filed: Oct. 3, 2017

(65) Prior Publication Data

US 2018/0084891 A1  Mar. 29, 2018

Related U.S. Application Data

(63) Continuation-in-part of application No. 15/279,603, filed on Sep. 29, 2016, now abandoned.

(51) Int. Cl.
| | |
|---|---|
| *B43K 27/02* | (2006.01) |
| *A45D 40/18* | (2006.01) |
| *A61C 15/04* | (2006.01) |
| *A45D 40/04* | (2006.01) |
| *A45D 40/24* | (2006.01) |
| *A45D 40/00* | (2006.01) |

(52) U.S. Cl.
CPC ............. *A45D 40/18* (2013.01); *A45D 40/00* (2013.01); *A45D 40/04* (2013.01); *A45D 40/24* (2013.01); *A61C 15/043* (2013.01); *A61C 15/046* (2013.01)

(58) Field of Classification Search
CPC ........ A45D 40/18; A45D 40/24; A45D 40/04; A61C 15/043; A61C 15/046
USPC ...................................................... 401/19, 52
See application file for complete search history.

(56) References Cited

U.S. PATENT DOCUMENTS

| | | | |
|---|---|---|---|
| 2,399,660 A | 5/1946 | Boulicault | |
| 4,934,389 A | 6/1990 | Pettiford | |
| 5,544,754 A | 8/1996 | Stahl | |
| 7,267,126 B1 | 9/2007 | Banegas | |
| 8,272,389 B2 | 9/2012 | Bish | |
| 9,498,311 B2 | 11/2016 | Kelchlin | |
| 2013/0020218 A1 | 1/2013 | Brilliant et al. | |
| 2013/0025614 A1 | 1/2013 | Morgan | |
| 2013/0252206 A1 | 9/2013 | Lee | |
| 2013/0320037 A1 | 12/2013 | Chovanec | |
| 2015/0245893 A1 | 9/2015 | Kelchlin | |

FOREIGN PATENT DOCUMENTS

| | | | |
|---|---|---|---|
| CA | 2444137 A1 | 4/2005 | |
| CN | 105326196 A | * | 2/2016 |
| CN | 105326196 A | 2/2016 | |

\* cited by examiner

*Primary Examiner* — Jennifer C Chiang
(74) *Attorney, Agent, or Firm* — Thompson Coburn LLP

(57) ABSTRACT

A lip balm container is presented as a tubular member having a hollow interior with axial opposite proximal and distal ends and a longitudinal axis extending between the proximal and distal ends. The tubular member has a first chamber in the hollow interior adjacent the proximal end, a dental floss cutting tool adjacent to the distal end, and a second chamber in the hollow interior intermediate the first chamber and the distal end. The first chamber receives lip balm and exposes the lip balm from the proximal end. The second chamber receives a coil of dental floss with a center axis of the coil of dental floss being arranged perpendicular to the lip balm container longitudinal axis. An aperture communicates with the second chamber and allows the lead end of the dental floss to advance from the second chamber to the dental floss cutting tool.

4 Claims, 4 Drawing Sheets

LIP BALM CONTAINER WITH DENTAL FLOSS DISPENSER

RELATED APPLICATION

This application is a continuation-in-part of U.S. patent application Ser. No. 15/279,603, filed on Sep. 29, 2016.

BACKGROUND AND SUMMARY

The disclosure relates to a lip balm container with dental floss dispenser.

DETAILED DESCRIPTION

Figure 1:
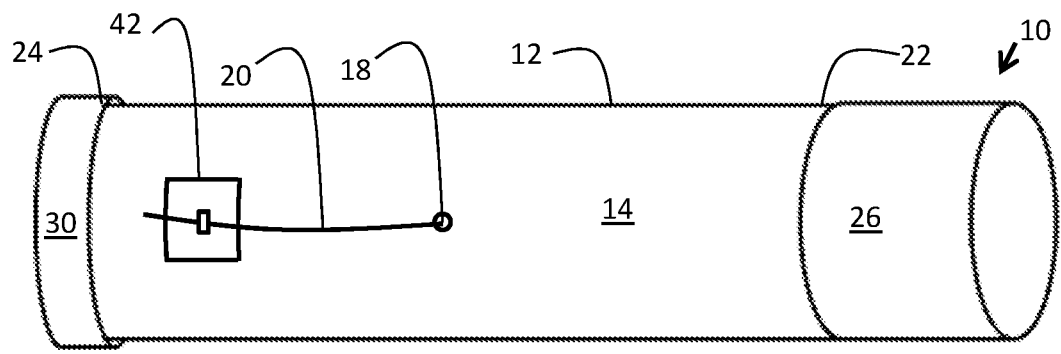
FIG. 1 is a perspective view of a side of a lip balm container as described herein showing dental floss extending from an aperture on the outer surface of the container to a dental floss cutting tool.

The lip balm container 10 may be formed from a tubular member 12 that has an outer surface 14 and a hollow interior 16. While the drawings show a cylindrical lip balm container, the tubular member is not intended to be limited to a circular cross section and other cross sectional shapes (square, triangle, rectangle, oval) may be used. The tubular member 12 may have an aperture 18 on its outer surface that communicates with the hollow interior 16. As will be explained, dental floss 20 disposed in the hollow interior of tubular member may be directed through the aperture 18 to allow it to be accessed by the user. The tubular member 12 may have axially opposite proximal and distal ends 22,24. The proximal end 22 may be configured to receive a cap 26 that is used to seal the lip balm container. Lip balm 28 may be advanced from the hollow interior 16 of the tubular member out the proximal end 22. The distal end 24 may include an operator 30. As explained below, the operator 30 may be operated to actuate a plunger 32 disposed in the hollow interior of the tubular member to advance the lip balm 28 from the tubular member proximal end. The operator 30 may be a dial operator which may be press fit into the distal end 24 of the tubular member. The operator 30 may be operatively connected to a spindle 34. The spindle 34 may be operatively connected to the plunger 32. Rotation of the operator 30 may in turn cause rotational movement of the spindle 34 and translation of the plunger 32 through the hollow interior of the tubular member so as to advance the lip balm 28 from the proximal end 22 of the tubular member 12. Although rotary motion of the spindle and operator may be used to advance the plunger, the operator may activate a ratcheting system for advancing the plunger, the operator may include a push button for advancing the plunger, or the operator may include an extension of the plunger for advancing the plunger.

Figure 3:
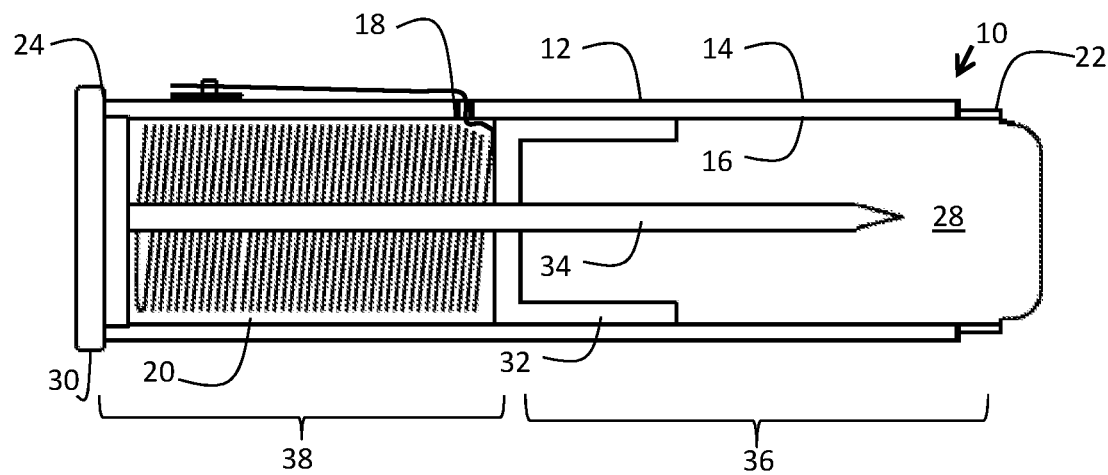
FIG. 3 is cross-sectional view of the lip balm container from a view similar to that of FIG. 2, showing a plunger, lip balm on one side of the plunger and dental floss on the other side of the plunger.

The plunger 32 may in part define a first chamber 36 within the hollow interior 16. The first chamber 36 may contain the lip balm. The plunger 32 may define a second chamber 38 within the hollow interior 16. As will be described in greater detail, the second chamber 38 may contain the dental floss 20. While FIG. 3 shows the plunger in part defining the second chamber for containing the dental floss, the second chamber may be in part defined by one or more walls (see '40' in FIG. 4) in the hollow interior that may be arranged between the plunger 32 and the distal end 24 of the tubular member 16. The dental floss 20 may be disposed in the volume between the wall(s) 40 and the distal end 24 of the tubular member.

The tubular member 12 may include a dental floss cutting tool 42 on its outer surface 14. The dental floss cutting tool 42 may be disposed between the aperture 18 and the distal end 24, and/or the operator 30. The dental floss cutting tool 42 may be spaced from the aperture 18 so as to allow a user to press the dental floss 20 with his or her finger against the outer surface 14 of the tubular member while grasping the free end of the dental floss and manipulating the dental floss against the cutting tool to cut the dental floss. The dental floss cutting tool 42 may be a projection extending from the outer surface 14 of the tubular member 12. The dental floss cutting tool 42 may be formed monolithically with the tubular member 12. The dental floss cutting tool 42 may be a separate member fixed to the outer surface 14 of the tubular member 12. The dental floss cutting tool 42 may be formed from a plastic or may be formed from a metal. The dental floss cutting tool 42 may be configured as is known in the art and used in connection with conventional dental floss containers. The dental floss cutting tool may be covered with a cap (not shown).

Figure 2:
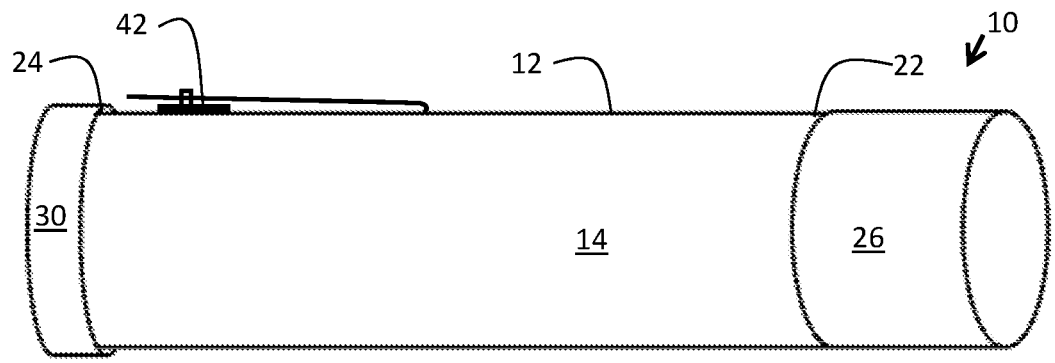
FIG. 2 is a perspective view of another side of the lip balm container of FIG. 1, providing additional detail of the dental floss cutting tool.
Figure 4:
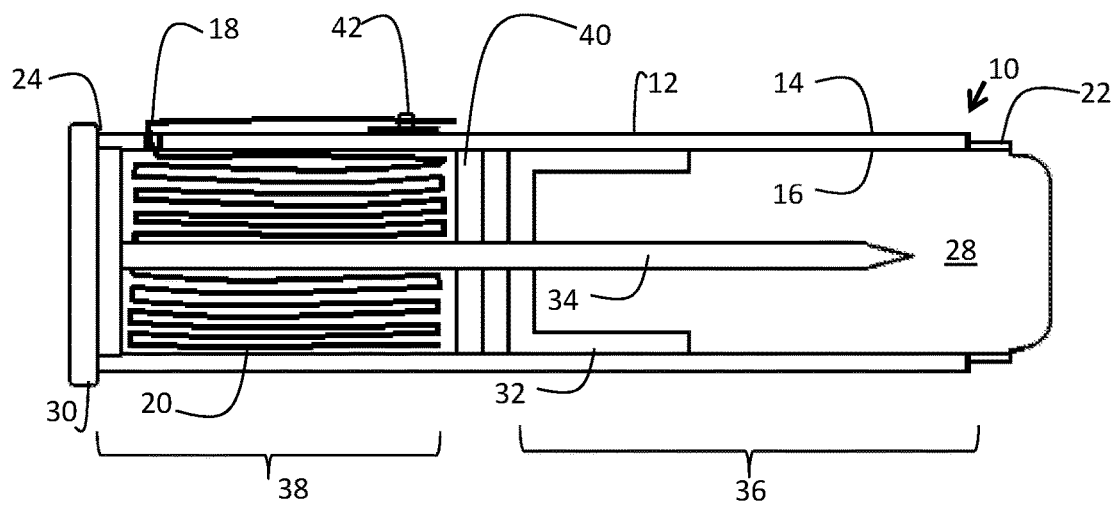
FIG. 4 is cross-sectional view of an alternate embodiment of a lip balm container showing a plunger, lip balm on one side of the plunger, a wall on the other side of the plunger, and dental floss between the wall and opposite end of the container.
Figure 5:
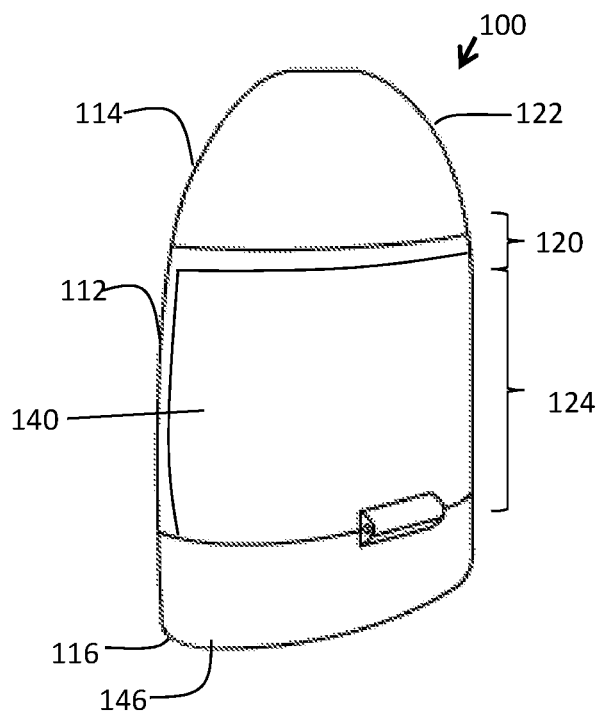
FIG. 5 is a perspective view of an alternate embodiment of a lip balm container.
Figure 6:
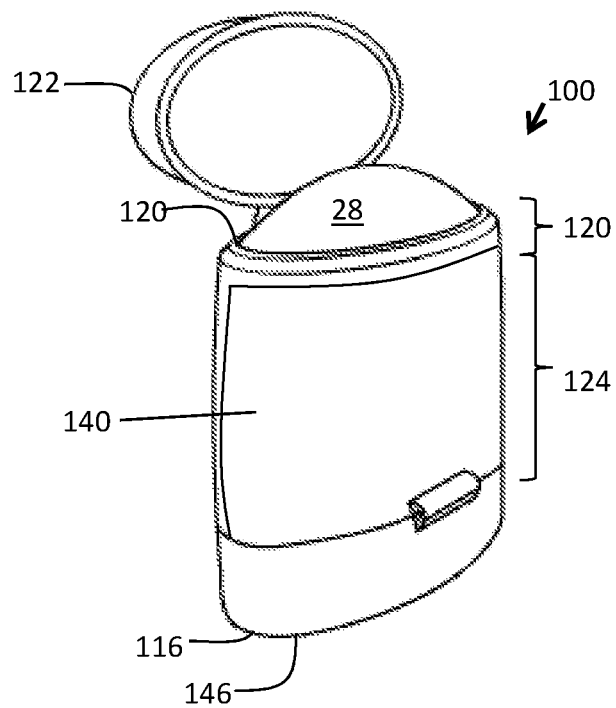
FIG. 6 is a perspective view of the lip balm container of FIG. 5 with a lip balm access cover open to expose lip balm of the lip balm container.

As is shown in FIGS. 2 and 3, the aperture 18 is arranged in a midsection of the tubular member 12 and the dental floss cutting tool 42 is disposed between the aperture and the distal end. As shown in the drawings, the aperture 18 is disposed on the tubular member 12 in a location between the dental floss cutting tool 42 and the proximal end 22. However, other arrangements may also be used, for instance as shown in FIG. 4, where the aperture 18 is adjacent to the distal end 24 of the tubular member 12 and the dental floss cutting tool 42 is in the midsection. The dental floss cutting tool 42 may also be provided on the operator.

The dental floss 20 may be disposed in the hollow interior of the tubular member in a location where it may be easily pulled out from the hollow interior of the tubular member. For instance, the dental floss may be arranged in a coil. The coil may have a center axis which is coaxially aligned with a center axis of the tubular member. The coil may extend around the spindle as shown in FIG. 3. The dental floss 20 may also be formed in a bundle which extends in a manner that traverses between the plunger 32 and the distal end 24 of the tubular member, for instance as shown in FIG. 4. The dental floss 20 may be disposed in the hollow interior of the tubular member in a manner so as to not interfere with the spindle 34 or operator 30. A starting end of the length of the dental floss may be arranged adjacent to the aperture 18. To protect the dental floss and maintain it in a hygienic state, the starting end of the dental floss may have a lead which may extend through the aperture 18 to the outside of the container. The lead may be trimmed with the dental floss cutting tool prior to a user using the dental floss. The lead allows the dental floss 20 to be extracted and pulled by the user from the hollow interior 16 and directed through the dental floss cutting tool 42. The dental floss cutting tool 42 may also secure the loose end of the dental floss so as to prevent inadvertent pulling of the dental floss 20 from the hollow interior 16 of the tubular member. The termination end of the length of the dental floss 20 may be placed adjacent to the distal end 24 of the tubular member and may be adjacent to the operator 30.

In preparing the lip balm container 10 for filling, the lip balm container may be provided to a filling entity (e.g., filling the lip balm and/or the dental floss) in the form of a blank or empty tubular member 12 with the plunger 32 positioned in an intermediate position in the hollow interior 16 of the tubular member. The spindle 34, operator 30, and cap 26 may be provided as a kit with the tubular member 12, and either fully or partly assembled with the tubular member and/or plunger. The tubular member 12 may be provided with the dental floss cutting tool 42 on the outer surface 14 of the tubular member. The tubular member 12 may be provided with the aperture 18. To the extent the spindle, operator and/or plunger are assembled with the tubular member, the operator may be manipulated so as to move the plunger to an intermediate position in the hollow interior of the tubular member. The lip balm 28 may be inserted into the hollow interior 16 of the tubular member 12 from the proximal end 22 adjacent to the plunger 32. The dental floss 20 may be inserted into the hollow interior 16 of the tubular member 12 from the distal end 24 by removing the operator 30 from the distal end of the tubular member. The starting end and/or the lead of the floss 20 may be directed from the hollow interior through the aperture. The operator 30 and/or spindle 34 may then be connected with the plunger 32 and reinstalled on the distal end 24 of the tubular member. The starting end and/or lead of the dental floss 20 may be secured to the outer surface 14 of the tubular member 12 with an adhesive and/or protective film. The cap 26 may be provided on the proximal end 22 of the tubular member and secured with an adhesive or protective film. The lip balm container 10 may include marketing information, personalized or corporate information, promotional material and other information on the outer surface 14. The information provided on the outer surface may assist in promoting an entity, the sale of the lip balm container, or other goods and services used in connection with the lip balm or dental floss.

FIGS. 5-8 show another embodiment of the lip balm container 100. The lip balm container 100 is presented as an oval cross-section shape, tubular member 112 with axially opposite proximal and distal ends 114,116 and a hollow interior 118. The lip balm 28 may be contained within a first chamber 120 within the hollow interior of the tubular member. The lip balm 28 may be exposed from the hollow interior 118 of the tubular member 112 from the proximal end 114. In the embodiment shown in FIGS. 5-8, the lip balm 28 is stationary in the hollow interior 118 of the tube and is not advanced with a plunger, although a plunger of the type described earlier could be provided. For instance, the first chamber 120 may be formed by inserting a concave or recessed member in the proximal end 114 of the tubular member 112 such that the concave member extends into the hollow interior of the tubular member. The amount concavity of the concave member is sufficient to hold an amount of lip balm 28 within the concave member and expose the lip balm for the user to use from the proximal end 114. The proximal end may be provided with a lip balm access cover 122. The lip balm access cover 122 may be hingedly connected, snap connected, or threadably connected to the lip balm container 110. The lip balm access cover 122 may be movable between an open position providing access to first chamber 120 and a closed position sealing the first chamber when not in use. To fill the first chamber 120 with lip balm 28, the lip balm access cover 122 may be moved to the open position. A concave member pre-filled with lip balm 28 may be press fit into the proximal end 114 of the tubular member 112, or the lip balm may be deposited in the concave member with the concave member installed in the proximal end of the tubular member. Once filled, the lip balm access cover 122 may be moved to the closed position. Thus, the lip balm access cover 122 may be movable between an open position providing access to the lip balm 28 and a closed position protecting the lip balm when not in use.

Figure 7:
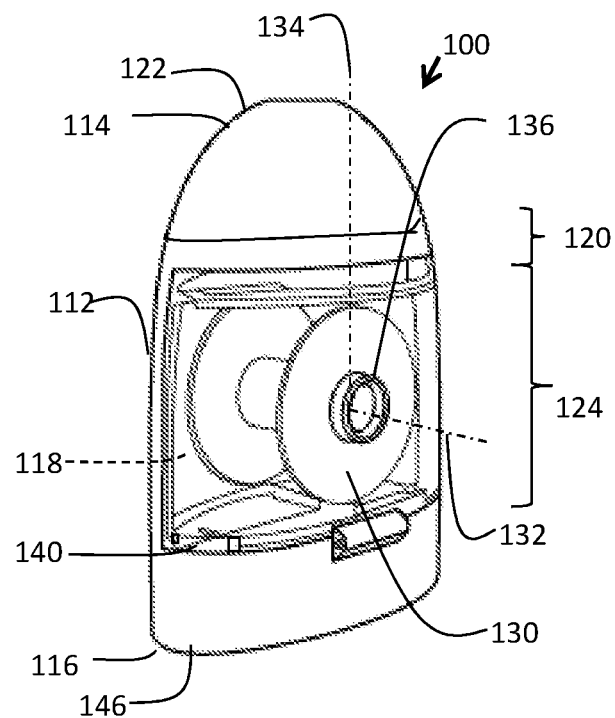
FIG. 7 is a perspective view of the lip balm container of FIG. 5 with side portions of the contained shown removed to further illustrate the arrangement of a coil of dental of the container.
Figure 8:
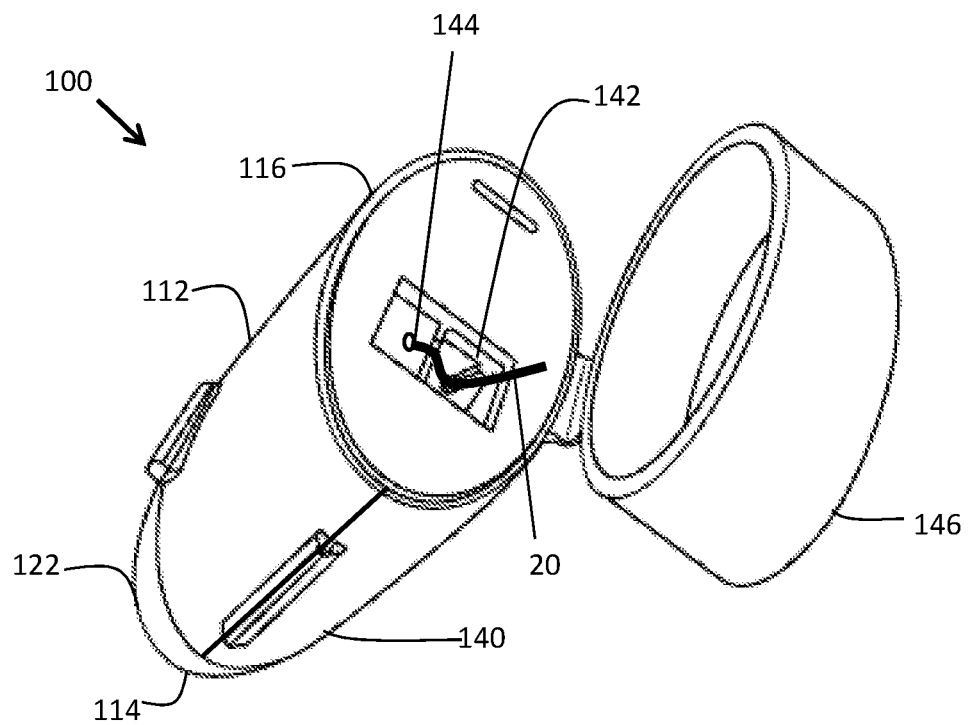
FIG. 8 is a perspective view of the lip balm container of FIG. 5 with floss access cover open to expose floss of the lip balm container.

In the hollow interior 118 of the tubular member 112 adjacent the first chamber 120, a second chamber 124 may be provided. The second chamber 124 may be configured to receive a coil 130 of dental floss 20. The coil 130 of dental floss 20 may be coiled in a cylindrical fashion. The second chamber 124 may be dimensioned to receive the coil 130 with the coil center axis 132 horizontal in FIG. 7 (e.g., perpendicular to the longitudinal axis 134 of the tubular member. While FIG. 7 shows the coil of dental floss 130 arranged with its center axis 132 perpendicular to the longitudinal axis 134 of the lip balm container 112, the coil of dental floss may have its center axis arranged parallel to the longitudinal axis of the container. The coil 130 may be mounted on an axle 136 within the second chamber 124 of the hollow interior 118 of the tubular member 112 so as to allow free rotation of the coil and dispensing of the dental floss from within the hollow interior of the tubular member of the lip balm container. A second chamber access cover 140 may be provided to allow access to the second chamber 124 for instance to install the coil 130 of dental floss 20. The second chamber access cover 140 may be hingedly connected to the lip balm container 110. The second chamber access cover 140 may be lockingly snap fit to the container 110 to limit access to the initial installation of the coil 130 of floss in the lip balm container, or the access cover may be repeatedly opened and closed as desired by the end user, for instance, to install a new dental floss coil after the initial preloaded coil is expended. The second chamber access cover 140 may be transparent while the remainder of the lip balm container 110 is opaque thereby exposing the coil 130 of dental floss to view to provide end user interest in the product. The second chamber access cover 140 may also be made from a material sufficiently translucent to allow viewing of the second chamber through the access cover.

At the distal end 116 of the tubular member 112, the lip balm container 110 may be provided with a dental floss cutting tool 142, for instance, in the manner previously described. The dental floss 20 from the coil 130 may be directed from the second chamber 124 of the hollow interior of the lip balm container through an aperture 144 disposed on the distal end 116 of the tubular member 112 adjacent to the dental floss cutting tool 142. The distal end 116 of the tubular member 112 may have a dental floss access cover 146. The dental floss access cover 146 may be hingedly connected to the lip balm container 110, snap connected, or threadably connected to the container. The dental floss access cover 146 may be movable between an open position providing access to the lead end of the dental floss 20 and a closed position protecting the lead end of the dental floss when not in use. Thus, in the open position, the dental floss access cover 146 may expose at least one of the aperture 144 and/or dental floss cutting tool 142, and in the closed position, the dental floss access cover may cover over at least one of the aperture and dental floss cutting tool.

The embodiments were chosen and described in order to best explain the principles of the disclosure and practical applications thereof to thereby enable others skilled in the art to best utilize the various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A lip balm container comprising:
    a tubular member having a hollow interior with axial opposite proximal and distal ends and a longitudinal axis extending between the proximal and distal ends, the distal end defining an axial face of the tubular member, the tubular member having a first chamber in the hollow interior adjacent the proximal end, the tubular member having a dental floss cutting tool disposed on an axial face of the distal end, the tubular member having a second chamber in the hollow interior intermediate the first chamber and the distal end;
    lip balm disposed in first chamber, the lip balm being stationary in the first chamber and exposed from the proximal end of the tubular member in a manner to be accessed by a user;
    a coil of dental floss disposed in the second chamber, the coil of dental floss having a center axis, the dental floss coil center axis being perpendicular to tubular member longitudinal axis; and
    an aperture disposed on the axial face of the distal end and spaced from the dental floss cutting tool, the aperture communicating with the second chamber through which a lead end of the dental floss is advanced toward the dental floss cutting tool;
    a dental floss access cover pivotally connectable to the tubular member adjacent to the distal end of the tubular member, the dental floss access cover being moveable between a closed position in which the dental floss access cover covers over the axial face of the distal end of the tubular member including the dental floss cutting tool and the aperture to protect the lead end of the dental floss when not in use, and an open position in which the dental floss access cover is spaced from the tubular member to provide access to the dental floss cutting tool and the lead end of the dental floss; and
    a lip balm access cover pivotally connectable to the proximal end of the tubular member, the lip balm access cover being movable between an open position providing access to the lip balm and a closed position protecting the lip balm when not in use.

2. The lip balm container of claim 1 further comprising a second chamber access cover movable between an open position providing access to the second chamber and a closed position sealing the second chamber wherein the second chamber access cover is made from a material sufficiently translucent to allow viewing of the second chamber through the access cover.

3. A lip balm container comprising:
    a tubular member having a hollow interior with axial opposite proximal and distal ends and a longitudinal axis extending between the proximal and distal ends with the distal end defining an axial face of the tubular member, the axial face of the distal end of the tubular member being perpendicular to the longitudinal axis, the tubular member having a first chamber in the hollow interior adjacent the proximal end, the tubular member having a dental floss cutting tool disposed on the distal end, the tubular member having a second chamber in the hollow interior intermediate the first chamber and the distal end, the first chamber being adapted and configured to receive lip balm in a manner such that the lip balm is stationary in the first chamber and the lip balm is exposed from the proximal end of the tubular member in a manner to be accessed by the user, the second chamber being adapted and configured to receive a coil of dental floss in the second chamber with a center axis of the coil of dental floss being arranged perpendicular to the lip balm container longitudinal axis, the tubular member having an aperture disposed on the distal end of the tubular member and spaced from the dental floss cutting tool and communicating with the second chamber;
    a dental floss access cover pivotally connectable to the tubular member adjacent to the distal end of the tubular member, the dental floss access cover being pivotable about an axis arranged in a direction parallel to a plane defined by the axial face of the distal end of the tubular member between a closed position in which the dental floss access cover covers over the distal end of the tubular member including the dental floss cutting tool and the aperture to protect the lead end of the dental floss when not in use, and an open position in which the dental floss access cover is spaced from the tubular member to provide access to the dental floss cutting tool and the lead end of the dental floss; and
    a lip balm access cover pivotally connectable to the proximal end of the tubular member, the lip balm access cover being movable between an open position providing access to the lip balm and a closed position protecting the lip balm when not in use.

4. The lip balm container of claim 3 further comprising a second chamber access cover movable between an open position providing access to the second chamber and a closed position sealing the second chamber wherein the second chamber access cover is made from a material sufficiently translucent to allow viewing of the second chamber through the access cover.

* * * * *